United States Patent
Lopath et al.

(10) Patent No.: US 10,548,772 B2
(45) Date of Patent: Feb. 4, 2020

(54) REAL TIME ACOUSTIC DOSIMETRY FOR CORNEAL COLLAGEN CROSSLINKING

(71) Applicant: TECLens, LLC, St. James, NY (US)

(72) Inventors: Patrick David Lopath, Stamford, CT (US); David E. Acker, St. James, NY (US)

(73) Assignee: TECLens, LLC, St. James, NY (US)

( * ) Notice: Subject to any disclaimer, the term of this patent is extended or adjusted under 35 U.S.C. 154(b) by 0 days.

(21) Appl. No.: 15/856,651

(22) Filed: Dec. 28, 2017

(65) Prior Publication Data

US 2018/0133055 A1 May 17, 2018

Related U.S. Application Data

(62) Division of application No. 14/751,324, filed on Jun. 26, 2015, now Pat. No. 9,883,970.

(Continued)

(51) Int. Cl.
*A61F 9/008* (2006.01)
*A61N 5/06* (2006.01)
(Continued)

(52) U.S. Cl.
CPC .......... *A61F 9/008* (2013.01); *A61B 8/0858* (2013.01); *A61B 8/10* (2013.01); *A61B 8/4236* (2013.01);
(Continued)

(58) Field of Classification Search
CPC .................. A61F 9/008; A61F 9/0079; A61F 2009/00842; A61F 2009/00844;
(Continued)

(56) References Cited

U.S. PATENT DOCUMENTS

| 2001/0016731 A1 | 8/2001 | DeVore et al. |
| 2006/0135957 A1 | 6/2006 | Panescu |

(Continued)

FOREIGN PATENT DOCUMENTS

| CN | 102917676 A | 2/2013 |
| CN | 103153396 A | 6/2013 |

(Continued)

OTHER PUBLICATIONS

He, Xiaoyin and Jun Liu, "A Quantitative Ultrasonic Spectroscopy Method for Noninvasive Determination of Corneal Biomechanical Properties," Investigative Ophthalmology & Visual Sci., vol. 50, No. 11 (Nov. 2009), pp. 5148-5154, copyright Association for Research in Vision and Ophthalmology.

(Continued)

*Primary Examiner* — Rex R Holmes
(74) *Attorney, Agent, or Firm* — Lerner, David, Littenberg, Krumholz & Mentlik, LLP

(57) ABSTRACT

A change in the response of the cornea to ultrasonic energy directed into the cornea is monitored during irradiation of the cornea to bring about corneal crosslinking. Because the change in ultrasonic response is correlated with the degree of crosslinking achieved, a desired degree of crosslinking can be achieved by terminating the irradiation when the change reaches a threshold. The change in ultrasonic response can be determined by taking a baseline measurement before irradiation and additional measurements during irradiation using the same ultrasonic transducer (47). The transducers may be carried on a device (30) resembling a contact lens which overlies the eye and which transmits the light used in the irradiation step to the eye.

5 Claims, 2 Drawing Sheets

Related U.S. Application Data

(60) Provisional application No. 62/096,164, filed on Dec. 23, 2014, provisional application No. 62/018,255, filed on Jun. 27, 2014.

(51) Int. Cl.
*A61B 8/10* (2006.01)
*A61F 9/007* (2006.01)
*A61B 8/08* (2006.01)
*A61B 8/00* (2006.01)

(52) U.S. Cl.
CPC ............ *A61B 8/485* (2013.01); *A61B 8/5207* (2013.01); *A61F 9/0079* (2013.01); *A61N 5/062* (2013.01); *A61F 2009/0088* (2013.01); *A61F 2009/00842* (2013.01); *A61F 2009/00844* (2013.01); *A61F 2009/00872* (2013.01); *A61F 2009/00897* (2013.01)

(58) Field of Classification Search
CPC .... A61F 2009/00897; A61F 2009/0088; A61F 2009/00872; A61B 8/5207; A61B 8/485; A61B 8/4236; A61B 8/0858; A61B 8/10; A61N 5/062
See application file for complete search history.

(56) References Cited

U.S. PATENT DOCUMENTS

| | | |
|---|---|---|
| 2008/0208177 A1 | 8/2008 | Mrochen et al. |
| 2009/0227909 A1 | 9/2009 | Schafer et al. |
| 2011/0237999 A1 | 9/2011 | Muller et al. |
| 2011/0282333 A1 | 11/2011 | Herekar et al. |
| 2012/0215155 A1 | 8/2012 | Muller et al. |
| 2013/0085370 A1 | 4/2013 | Friedman et al. |
| 2013/0211389 A1 | 8/2013 | Chuck et al. |
| 2014/0379054 A1 | 12/2014 | Cooper et al. |
| 2015/0005750 A1* | 1/2015 | Kelleher ............ A61F 9/00802 606/3 |

FOREIGN PATENT DOCUMENTS

| | | |
|---|---|---|
| DE | 102008046834 A1 | 3/2010 |
| EP | 1561440 A1 | 8/2005 |
| WO | 2009073213 A1 | 6/2009 |
| WO | 2013106385 A2 | 7/2013 |
| WO | 2016106210 A1 | 6/2016 |
| WO | 2016106217 A1 | 6/2016 |

OTHER PUBLICATIONS

International Search Report and Written Opinion for Application No. PCT/US2015/038031 dated Dec. 14, 2015.

International Search Report and Written Opinion for International Application No. PCT/US2015/038031, dated Apr. 14, 2016.

Mansouri et al., A Minimally Invasive Device for the Monitoring of 24-hour Intraocular Pressure Patterns, US Ophthalmic Review 6(1):10-14 (2013.

Chinese Search Report for CN Application No. 2015800449051, dated Jul. 3, 2018.

Zhang et al., "Preliminary Study on the Effect of Stiffness on Lamb Wave Propagation in Bovine Corneas", In Engineering in Medicine and Biology Society (EMBC), 2013 35th Annual International Conference of the IEEE, Jul. 2013, pp. 1120-1123.

* cited by examiner

REAL TIME ACOUSTIC DOSIMETRY FOR CORNEAL COLLAGEN CROSSLINKING

CROSS-REFERENCE TO RELATED APPLICATIONS

The present application is a divisional application of U.S. patent application Ser. No. 14/751,324, filed Jun. 26, 2015, now U.S. Pat. No. 9,883,970, which application claims the benefit of the filing date of U.S. Provisional Patent Application No. 62/096,164, filed Dec. 23, 2014, and also claims the benefit of the filing date of U.S. Provisional Patent Application No. 62/018,255, filed Jun. 27, 2014. The disclosures of the foregoing applications are hereby incorporated by reference.

BACKGROUND OF THE INVENTION

The present invention relates to methods and apparatus for corneal collagen crosslinking ("CCXL").

The vision of a human or other mammalian subject can be modified by crosslinking the collagen within the cornea of the eye. A photoactivated crosslinking facilitator such as riboflavin is applied to the cornea. Light at a wavelength selected to activate the crosslinking facilitator is applied. Where the crosslinking facilitator is riboflavin, the light typically is ultraviolet or blue light. The activated facilitator causes crosslinking of the collagen within the cornea. The crosslinking changes the mechanical properties of the cornea. For example, the crosslinking stiffens the cornea. These changes can result in stabilization of pathological conditions, such as keratoconus, or in alterations to the shape of the cornea. This technique can be used to correct defects in vision such as myopia, hyperopia, or astigmatism. For myopia (nearsightedness), the center of the cornea is stiffened; for hyperopia (farsightedness), an annulus around the periphery of the cornea is stiffened. For more complicated corrections such as astigmatism, custom patterns are used.

In some applications, the light is applied as a beam directed into the eye from a device remote from the eye. In other applications, the light is applied by a device which rests on the eye. As disclosed in U.S. Patent Application Publication No. 2014/0379054 ("the '054 Publication") and U.S. Provisional Patent Application No. 61/839,016 ("the '016 Provisional"), the disclosures of which are hereby incorporated by reference herein, light can be applied to the eye through a structure having a form, size, and shape resembling that of a contact lens such as a scleral contact lens. The structure may incorporate an optically dispersive element. Light may be directed into the dispersive element and dispersed so that the dispersed light passes into the eye from the dispersive element. This arrangement has numerous advantages. For example, the patient may be able to close his or her eye during the treatment, so that the structure is disposed between the eyelid and the eye.

CCXL changes the mechanical properties of the cornea by creating chemical bonds between the protein layers in the corneal stroma. These bonds (crosslinks) increase the stiffness of the cornea in the region crosslinked. This increased stiffness changes the balance between the cornea tension and the intraocular pressure. Through mechanisms not completely understand in the field, within a few days to weeks of CCXL therapy, physiologic processes reshape the cornea. The amount of reshaping, and thus the degree of curvature correction, is determined by a number of treatment parameters, including the amount and rate of energy delivery, the treatment time and the aperture of the treated area on the cornea. The amount of reshaping also may be influenced by factors such as the oxygen saturation of the cornea during irradiation; the amount of crosslinking facilitator present in the cornea during irradiation and physiological differences between patients.

As with any therapeutic energy delivery modality, it is desirable to control the irradiation of the eye so as to deliver a dose of radiation which will yield the desired procedural outcome, such as a desired degree of reshaping. Because numerous factors control the relationship between the light energy applied to the cornea during irradiation and the amount of reshaping achieved, it is difficult to achieve a precise degree of reshaping by selecting a dose of energy in advance, based on a priori knowledge of a relationship between dose and reshaping, and then simply applying the selected dose.

The reshaping of the cornea after CCXL takes place over a few days to weeks after the procedure. Thus, the real time monitoring of corneal shape during irradiation cannot be used as a measurement during the procedure to control the dose of UV delivered.

It has been proposed to use Brillouin microscopy to monitor properties of the cornea in conjunction with corneal crosslinking. However, application of this approach in a clinical setting suffers from significant practical difficulties.

Accordingly, further improvement would be desirable.

SUMMARY OF THE INVENTION

One aspect of the present invention provides methods of corneal crosslinking. A method according to this aspect of the invention desirably includes the step of irradiating a cornea in an eye of a living subject with light to induce crosslinking of collagen in the cornea. The method desirably further includes the step of monitoring the crosslinking by directing ultrasonic energy into the cornea and determining a response of the cornea to the ultrasonic energy using one or more transducers. The steps of directing ultrasonic energy and determining a response most preferably are using the same one or more transducers to provide a baseline response before commencement of the light applying step and one or more additional responses during the light applying step. The method desirably further includes the step of comparing the additional responses to the baseline response and controlling the irradiating step based at least in part on the results of the comparison. For example, the controlling step may include terminating the irradiation when a comparison between an additional response and the baseline response indicates a change in the response in excess of a threshold value. Most preferably, the one or more transducers used to direct ultrasonic energy into the cornea and to determine the response are mounted on a structure which overlies the anterior surface of the eye and rests on the eye during the irradiating and monitoring steps. The structure desirably is adapted to transmit the light used in the irradiating step. For example, the structure may be a structure such as that described in the '054 Publication.

The various elastic moduli of the cornea are fundamental material properties of the cornea. In conjunction with forces which act on the cornea, such as intraocular pressure, the elastic moduli determine the shape of the cornea. The elastic moduli change during crosslinking, and thus change in the elastic moduli is correlated with the degree of crosslinking. In preferred methods according to this aspect of the invention, the response of the cornea to ultrasonic energy, alone or in conjunction with other data, serves as a "proxy" for one or more of the material properties of the cornea, such as one or more of the elastic moduli. As referred to herein, a "proxy" for one or more material properties is a value or set of values which changes in a manner correlated to the material properties. As properties of the collagen in the cornea such as the elastic moduli of the collagen change during crosslinking, the proxy indicates the degree of crosslinking. Thus, the baseline response determined prior to irradiation is a proxy for the original material properties, whereas each additional response is a proxy for the material properties at a time during irradiation. Comparison of the proxy determined during irradiation with the original or baseline proxy gives an indication in the change in material properties, and thus an indication of the degree of crosslinking which has occurred. It is not essential to determine the actual material properties. Moreover, because the same transducer or transducers mounted on the same structure overlying the eye are used for both baseline and additional measurements, the same errors will affect both baseline and additional measurements. Therefore, these errors will be substantially cancelled in the comparison between the baseline and additional proxies.

As further discussed below, several different responses to applied ultrasonic energy can be used. These include the spectrum of backscattered ultrasonic energy, the time of flight of reflected ultrasonic pulses; and the resonant frequency or period of the cornea after it is displaced from its rest position by applied ultrasonic energy.

Further aspects of the present invention provide methods of measuring a physical property of the cornea in a living subject, as well as devices and systems which can be used in such methods and in the method of corneal crosslinking discussed above.

DETAILED DESCRIPTION

Figure 1:
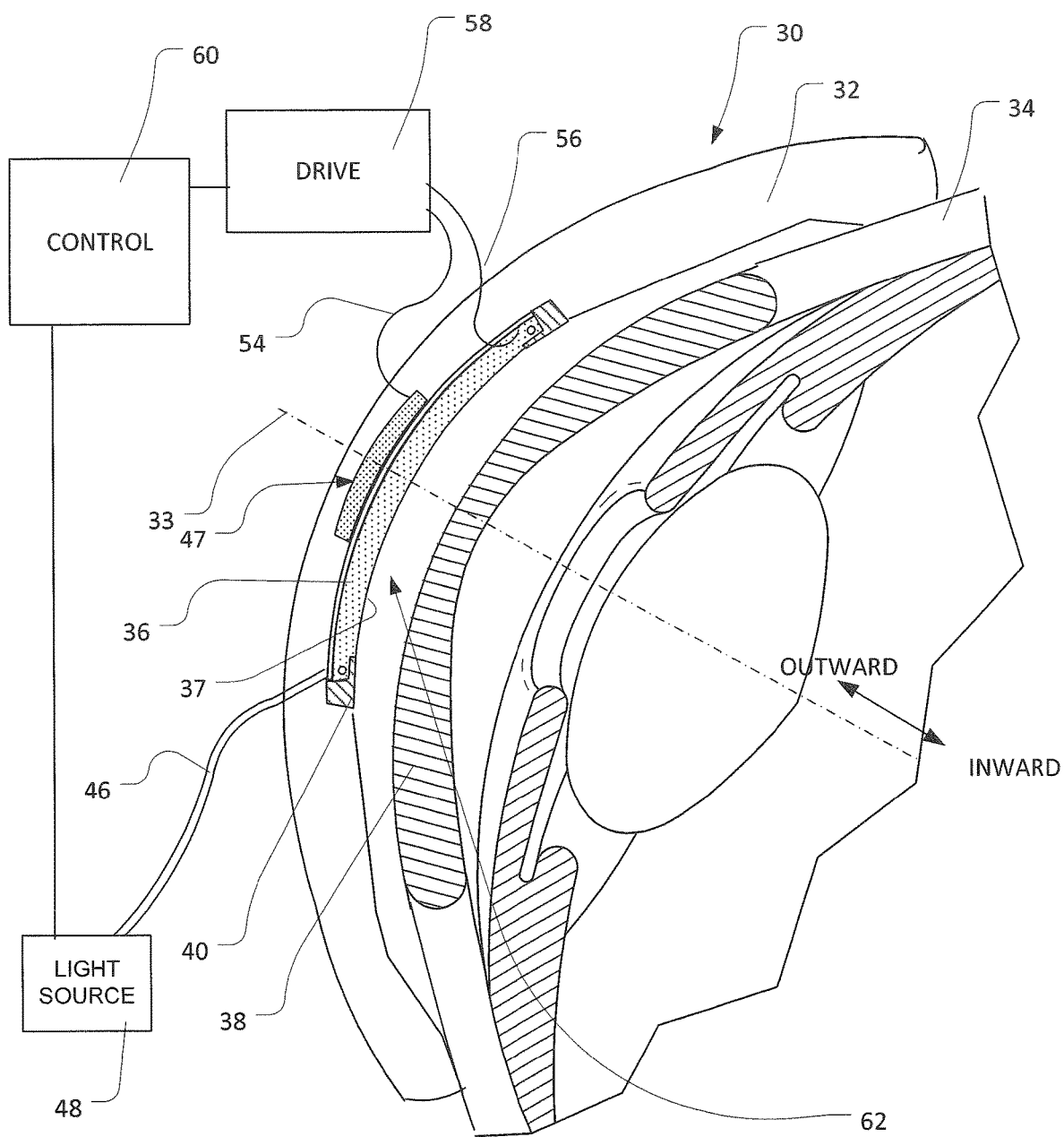
FIG. 1 is a diagrammatic sectional view depicting elements of a system according to one embodiment of the invention in conjunction with an eye of a subject.
Figure 2:
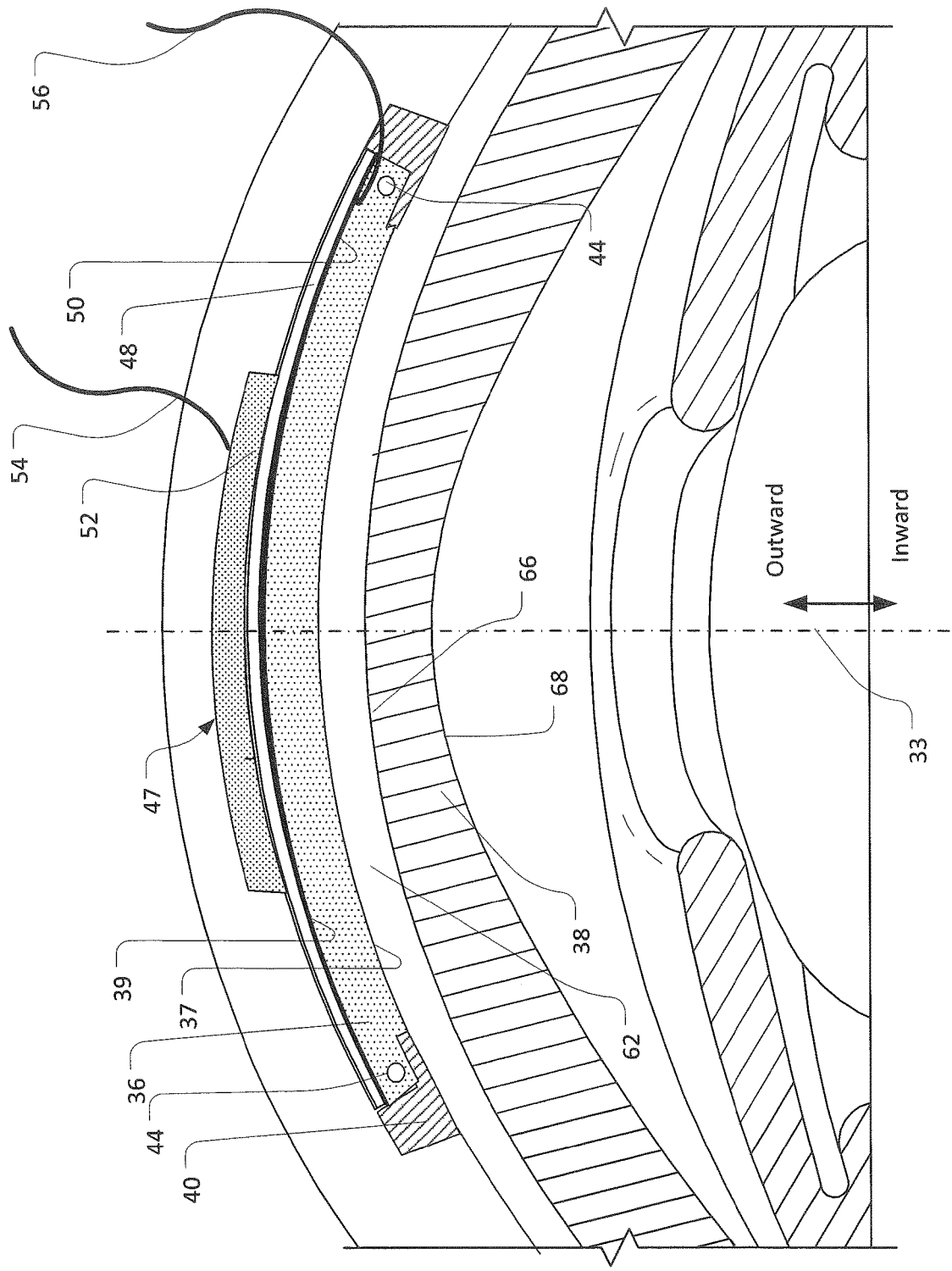
FIG. 2 is a fragmentary sectional view on an enlarged scale depicting elements of the system shown in FIG. 1.

A system according to one embodiment of the invention includes a device 30 having a structure adapted to overlie and rest upon the anterior surface of the eye. The structure of the device includes a housing 32 generally in the form and size of a scleral contact lens having a central axis 33. The housing includes a peripheral portion adapted to bear on the sclera 34 of the eye when the device is in place on the eye as depicted in FIG. 1. When the device is in place on the eye, the central axis 33 of the housing is aligned with the cornea 38 of the eye and the axis 33 extends inwardly toward the eye and outwardly away from the eye. The structure further includes a diffuser 36 disposed in a central portion of housing. As described in greater detail in the '054 Publication, the diffuser is formed from an optically dispersive material such as a clear silicone polymer with particles such as titanium dioxide dispersed therein. The diffuser may be in the form of a layer or dome having an inner surface 37 facing toward the eye when the structure is in place. The structure further includes a fiber carrier 40 defining an aperture aligned with a portion of the diffuser 36. In the particular embodiment depicted, the aperture is in the form of a circular opening as, for example, about 6 mm in diameter, although other sizes and shapes may be employed. As best seen in FIG. 2, one or more optical fibers 44 extend within the fiber carrier 40 and are in optical communication with the diffuser 36. The optical fibers 44 are connected via a transmission fiber or fibers 46 (FIG. 1) to a light source such as a laser 48. The foregoing features of the device may be as disclosed in the '054 Publication, and may also include the features disclosed in U.S. Provisional Patent Application No. 62/095,416, filed Dec. 22, 2014 ("the '416 Provisional"), the disclosure of which is hereby incorporated by reference herein.

The device further includes an ultrasonic transducer 47 incorporating a layer 48 of a piezoelectric material, preferably a polymeric piezoelectric material such as polyvinylidene fluoride ("PVDF") or other piezoelectric polymer, co-polymer, or composite. An electrically conductive metallic film 50 such as an aluminum film overlies an inner or front surface of the piezoelectric layer. The metallic film may be a film formed by vapor deposition on the piezoelectric layer or a thin foil in contact with the piezoelectric layer. The metallic film may be provided with a thin layer of a coating to prevent oxidation of its surface as, for example, a deposited $SiO_2$ coating. The surface of the metallic film abuts the rear or outer surface 39 of the diffuser. Desirably, the metallic layer covers the entire outer surface 39 of the diffuser. As further discussed below, the metallic layer acts both as an electrode of transducer 47 and as a reflector for light.

A backing layer 52 abuts the rear or outwardly-facing surface of the piezoelectric film 48 in a region of the film. Backing layer 52 is formed from a material which desirably has acoustic properties approximating those of air. Desirably, the material is acoustically attenuative or "lossy" at acoustic frequencies in the ranges discussed herein. The material of the backing layer desirably has acoustic impedance lower than the acoustic impedance of the piezoelectric layer and also lower than the acoustic impedance of the diffuser. For example, the backing may be a foam such as syntactic foam incorporating hollow "microballoons" and an adhesive matrix. Desirably, the backing is also electrically conductive. The microballoons may incorporate or may be coated with an electrically conductive material such as silver. Alternatively or additionally, the adhesive matrix may be an electrically conductive polymer or may incorporate an electrically conductive material as, for example, silver particles. The electrically conductive backing layer 52 and the metallic film 50 serve as electrodes for the piezoelectric film 48 in the region covered by the backing layer. Electrical connections schematically indicated at 54 and connect the electrodes 50 and 52 to a drive circuit 58 (FIG. 1). As discussed further below, the drive circuit 58 is arranged to excite the piezoelectric film 48 to emit ultrasound and to receive electrical signals generated by the piezoelectric film responsive to ultrasound impinging on the film.

Desirably, the ultrasonic transducer is a high-frequency transducer, capable of operating efficiently at frequencies of 10 MHz or more, preferably 20 MHz or more, more desirably 50 MHz or more, and most desirably 100 MHz or more.

The foam backing 52 helps to ensure acoustic isolation of the transducer from the structure behind it. These balloons are very low density. The low density foam created from the microballoons does not load the acoustic transducer as much as the front layers of the light guide and beyond. Thus, the larger real load on the front of the acoustic transmitter enables a larger forward transmitting voltage response (TVR) than rearward TVR, so more energy is transmitted forward (in the inward direction indicated in FIG. 2) than backward. This helps reduce the rear reflections that must be attenuated, helping to prevent confounding signals from reflecting off backing interfaces and returning to the transducer. The ultimate goal of this foam backing is to approximate air, which is highly attenuative at high frequencies. In addition to poor coupling to (and thus power transfer from) the transducer and limited ability to support high frequency compressional waves, the very light backing foam also contains scatters (microballoons and potentially silver particles from a conductive epoxy used as the adhesive matrix) of various sizes on the order of the acoustic wavelength. This scattering helps to further attenuate any rearward waves before they can reflect back to the transducer. The light foam (or air) backing has the added benefit of improving the sensitivity of the transducer in receive mode by enabling impinging waves that are returning from the region of interest to dissipate most of their energy in the piezoelectric material, as opposed to traveling through the sensor into the backing.

The diffuser 36 constitutes the load on the front or inward-facing side of the piezoelectric film. The material of the diffuser has an acoustic impedance close to that of the polymeric material of the transducer. The matching acoustic impedance promotes efficient emission from the front or inward-facing surface of the transducer, and efficient transfer to the transducer of ultrasonic signals returning through the diffuser from the eye. The transducer and optical elements of the device, including the diffuser 36 and the aperture defined by fiber carrier 40 are arranged so that at least part of the region exposed to ultrasonic energy from the transducer lies within the region exposed to light supplied by the optical elements. In the particular arrangement shown, the transducer and is coaxial with the optical elements. The optical elements are arranged to apply light to a circular region of the cornea surrounding the central axis 33 of the device, and the ultrasonic transducer is arranged to apply ultrasound to a circular region surrounding the same axis.

The drive circuit 58 (FIG. 1) includes conventional components for generating high-frequency electrical signal and supplying the same to the transducer. The drive circuit also includes conventional components for receiving electrical signals from the transducer and providing representations of those signals. For example, the drive circuit may include components such as analog to digital converters, digital to analog converters, an oscillator, amplifiers and filters.

A control circuit 60 is connected to drive circuit 58, so that the control circuit can command the drive circuit and transducer to apply ultrasound and so that the control circuit can receive representations of signals generated by the transducer responsive to ultrasound impinging on the transducer. The control circuit 60 is also connected to light source 48 so that the control circuit can control operation of the light source. The control circuit may include a general-purpose computer having elements such as a processor, a memory linked to the processor and input/output elements. The memory desirably stores instructions operative to cause the computer to execute the operations discussed below.

When the device 30 is in disposed on the eye in the operative position shown in FIG. 1, there is a space 62 between the anterior surface of the cornea 38 and the inner surface 37 of the diffuser. This space 62 desirably is kept filled with a liquid during operation of the device. The liquid desirably is transparent to the light such as UV which will be applied by the device, and desirably has acoustic impedance reasonably close to that of the diffuser 36 and the cornea 38. For example, an aqueous liquid such as a saline solution or the subject's natural tears may fill the space. Preferably, the liquid disposed in space 62 desirably contains a source of oxygen, as disclosed in U.S. Provisional Patent Application No. 62/095,288, filed Dec. 22, 2014, ("the '288 Provisional") the disclosure of which is hereby incorporated by reference herein. As disclosed in the '288 Provisional, the oxygen source helps to maintain oxygen saturation of the cornea during the crosslinking procedure, and thus promotes crosslinking. As also disclosed in the '288 Provisional, pharmaceutically acceptable perfluorocarbons can serve as a source of oxygen and be used as a part or all of the liquid. Use of a perfluorocarbon liquid is particularly advantageous where ultrasonic energy is to be applied to the cornea. Perfluorocarbons are dense and transmit both UV light and ultrasound well.

In a method according to one embodiment of the invention, the transmission time of ultrasound within the cornea serves as a proxy for the stiffness or elastic modulus of the cornea. In a method according to this embodiment, the cornea is pre-treated by exposure to a liquid containing a photoactivated crosslinking facilitator such as riboflavin. As disclosed in the '288 Provisional, this liquid also may contain an oxygen source to increase the oxygen saturation of the cornea prior to irradiation. The liquid containing the facilitator is typically is confined on the eye by a device. This device may be the device discussed above, or may be another device such as a contact lens.

Once the cornea has been brought to the desired riboflavin saturation, and the device discussed above is in place with a suitable liquid disposed in space 62, but before irradiation of the cornea, the control circuit 62 obtains an initial response of the cornea based on travel time of ultrasound through the cornea. To do so, the control circuit actuates the drive circuit 58 to apply very brief pulses of a positive or negative potential to transducer 47. Each pulse of the electrical potential desirably is a single, high frequency content potential spike. Each pulse of the potential causes the piezoelectric film 48 to vibrate and emit a brief pulse of ultrasound having a broad bandwidth. The ultrasound pulses travel along a forward path, in the inward direction through the diffuser 36 and through the liquid in space 62 to the cornea 38. A portion of each ultrasound pulse will be reflected at the anterior or outward-facing surface 66 of the cornea, but the remainder of the pulse will continue along the forward path to the posterior or inward-facing surface 68 of the cornea, where another portion of the pulse is reflected. The reflected pulses travel along a reverse path, outwardly through the liquid in space 62 and the diffuser and back to the transducer 47. As the pulses impinge on the piezoelectric film 48, the transducer produces electrical signals at frequencies corresponding to the frequencies of the ultrasonic energy. These signals are received by the drive circuit 58 (FIG. 1).

Each pulse reflected from posterior surface 68 is delayed relative to the corresponding pulse reflected from anterior surface 66. This delay is caused by the time required for the ultrasound to travel forwardly from the anterior surface 66 to the posterior surface 68, and the additional travel time required for the reflected pulse for travel in the reverse direction from the posterior surface to the anterior surface. Stated another way, the delay or difference in arrival times between anterior surface reflections and posterior surface reflections is equal to the transmission time required for the ultrasound to travel twice through the cornea. This transmission time is equal to twice the thickness of the cornea divided by the speed of sound in the material constituting the cornea. The speed of sound in the cornea is directly related to the stiffness of the material constituting the cornea and in particular to the Young's modulus (elastic modulus in tension or compression). Therefore, this transmission time is inversely related to the Young's modulus and directly related to the thickness of the cornea. The control circuit 60, in cooperation with the drive circuit 58, determines the transmission time and records it as a baseline response of the cornea. The transmission time may be recorded either directly as a value of time or indirectly, after conversion of the transmission time to some other representation. For example, the transmission time can be converted to an estimated elastic modulus based an assumed or measured thickness of the cornea, or converted to an estimated thickness of the cornea based on an assumed elastic modulus. Desirably, the process of determining the transmission time is repeated using multiple transmitted pulses to arrive at an average value of the baseline response.

After the baseline response has been obtained, the control circuit actuates the light source 48 (FIG. 1) to direct light such as UV light into the cornea through the device. As discussed in greater detail in the '054 Publication and '416 Provisional, the light passes through the transmission fiber 46 and to the fiber or fibers 44 in the device, and then passes into the diffuser, in directions generally toward the central axis 33. As the light passes through the diffuser, it is dispersed. Some of the dispersed light is directed inwardly toward the cornea. Dispersed light directed outwardly will be reflected inwardly by the metallic coating 50 (FIG. 2) overlying the outer surface of the diffuser, and thus will be redirected inwardly toward the cornea. The inwardly-directed light passes through the liquid in space 62 and irradiates the cornea. This light, in conjunction with the crosslinking facilitator present in the cornea, causes crosslinking of collagen in the irradiated area of the cornea. The irradiation step may use either continuously-applied light or light applied in pulses, typically a few seconds to a few minutes long.

During the irradiation process, the control circuit actuates the drive circuit and transducer 47 to acquire transmission times as additional responses of the cornea. Each additional response is acquired in the same manner as the baseline response discussed above, using the same transducer. Here again, each additional response represents the transmission time of ultrasound through the cornea in forward and reverse directions. The ultrasound used in acquiring the responses does not interfere with the light used in the irradiation. Thus, the additional responses can be acquired during the irradiation step, regardless of whether the irradiation is continuous or pulsatile. If the irradiation is pulsatile, the additional responses can be obtained during or between irradiation pulses, or at times unrelated to the pulsing cycle, so that the times when additional responses are acquired have a random relationship to the irradiation pulses. Each additional response may include averaged results from multiple pulses within an interval which is short in comparison to the total length of the irradiation process.

The control circuit compares each additional response to the baseline response. For example, the control circuit may determine the difference between the baseline transmission time and each additional transmission time. This difference represents a change in the properties of the cornea induced by the irradiation. When the difference reaches a preselected threshold, the control circuit terminates the irradiation. The threshold may be a function of the baseline response. For example, the threshold may be a certain percentage decrease from the baseline transmission time. The computation of the difference between the additional transmission time and the baseline transmission time may be performed implicitly, without an explicit subtraction operation. For example, the threshold may be stored in the control circuit as a value representing the baseline transmission time minus the preselected percentage decrease, and each additional transmission time may be compared with this value. In this instance, if an additional response is lower than this value, the control circuit terminates the irradiation step. In some cases, a decrease in transmission time on the order of 10-20% may correspond to the degree of crosslinking needed to bring about a desired reshaping of the cornea. Changes of this magnitude can be measured readily.

The additional responses are obtained in real time, during the irradiation step, so that the system can control the irradiation process based on the comparison as discussed above. Because the difference in the response vis-à-vis the baseline response arises directly from the effects of the crosslinking process, this difference is closely correlated with the degree of crosslinking achieved by the irradiation. Therefore, it is closely correlated to the magnitude of change in the shape of the cornea which will occur in the corneal reshaping process which occurs after the irradiation step. For example, the relationship between magnitude of shape change and the threshold can be compiled based on experience with experimental subjects, and can be continually updated as further experience is gained with clinical patients. This relationship can be stored in the control system as, for example, as a lookup table. The physician may specify a desired shape change, and the control system may select the appropriate threshold using the stored relationship.

The comparison between the baseline response and the additional response cancels out systematic errors. For example, misalignment between the transmission direction of the ultrasound and the thickness dimension of the cornea may exaggerate or diminish the measured transmission time. In the method discussed above, the transmission time is measured using the same transducer, mounted on a structure remains in fixed place on the eye throughout both the baseline and additional measurements. Thus, any error in the transmission time will affect both the baseline response and the additional response. The thickness of the cornea, as well as the elastic modulus, may change during irradiation as a result of the crosslinking. The transmission time measurement does not discriminate between change in elastic modulus and change in thickness. However, because both effects are correlated with crosslinking, the correlation between change in transmission time and degree of crosslinking is still valid.

Desirably, the wavelength of the ultrasound used in the transmission time measurement is small in comparison to the thickness of the cornea. Desirably, the ultrasound has a frequency of at least 20 MHz, more desirably at least 50 MHz, and most desirably at least 100 MHz Transducers formed from thin layers of piezoelectric polymers are well suited to operation at these frequencies. Moreover, the entire transducer, including the polymeric film and the backing element, may be on the order of less than a millimeter to a few millimeters thick. The transducer is thus well-suited to incorporation in a device resembling a contact lens. The leads connecting the electrodes of the transducer to the drive circuit typically introduce some inductance into the electrical system. However, the transducer has substantial capacitance. Desirably, the inductance and capacitance are selected so that the electrical impedance of the transducer and leads taken together matches the output impedance of the drive circuit component used to excite the transducer and matches the input impedance of the drive circuit component that receives electrical signals from the transducer.

The pulses used for measuring transmission time should be as brief as possible while still providing as high an amplitude as possible reflected pulses with an adequate signal to noise ratio. For example, each pulse may approximate a pulse of two cycles at 50 to 100 MHz. Because the bandwidth of a pulse is directly related to the pulse length, such a pulse will have a broad bandwidth.

A further embodiment of the invention may use the same device as discussed above, and the same process of treating the cornea with a crosslinking facilitator and providing a liquid in the space 62 between the device and the eye of the subject. The system used in this method also incorporates a light source, and drive circuit as discussed above, as well as a control circuit similar to the control circuit discussed above connected to the drive circuit and light source. In this embodiment, however, the drive circuit is arranged to determine the natural frequency or period of vibration of the cornea in the manner discussed below as a response of the cornea which is related to the degree of crosslinking.

The natural frequency, $f_0$, of any vibrating system is related to the stiffness of through:

$$f_0 \propto \sqrt{(k/m)} \quad \text{(Formula 1)}$$

where k is the stiffness constant and m is the effective mass of the system. The Young's modulus or elastic modulus of a material can be thought of as k for a unit area and unit length. The cornea can be thought of as membrane. As the elastic modulus increases, the stiffness of the membrane increases, and the natural frequency of vibration of the membrane increases. It has been estimated that crosslinking which is effective to correct vision and treat keratoconus will increase the elastic modulus of the cornea on the order of about 50% to 80%. Applying Formula 1 above, an 80% increase in the elastic modulus translates to about a 35% increase in $f_0$.

To acquire a measurement of the natural frequency or period of vibration, the control circuit first commands the drive circuit and transducer to apply a pulse of ultrasound, desirably at a frequency above about 20 MHz, such as 50-100 MHz or more, to a location on the cornea. This pulse is referred to herein as a "push pulse." Desirably, the push pulse is gated by a square wave, so that the amplitude of the ultrasound increases rapidly at the inception of the pulse and decreases rapidly at the end of the pulse. The push pulse propagates in a longitudinal direction into the cornea. In the particular embodiment depicted, where the transducer is centered on the central axis 33 of the device, the pulse may propagate inwardly along the axis. The inwardly propagating pulse is attenuated to some degree by the cornea. As the pulse is attenuated by the cornea, it transfers momentum to the cornea, and thus applies a longitudinal force to the cornea. This force displaces the part of the cornea where the pulse is applied in the longitudinal direction. Stated another way, the pulse acts to apply a force having a component perpendicular to the surface of the cornea. The magnitude F of this force is given by:

$$F = 2\alpha I/c \quad \text{(Formula 2)}$$

where $\alpha$ is attenuation, I is intensity and c is the longitudinal speed of sound.

The force deforms the cornea, effectively pushing the cornea inwardly at the location where the push pulse is applied. Stated another way, the force applied by the push pulse mechanically excites the cornea by deforming it from a rest position. When the push pulse ends, the cornea rebounds. The cornea will rebound and oscillate at its natural frequency. Transverse waves (waves propagating in a direction approximately perpendicular to the direction of the wave amplitude) propagate out from the location where the push pulse was applied. The propagation pattern resembles the propagation of ripples on a pond. This is the classic "step function response" of a membrane, although in this case, the membrane (the cornea) is curved.

The control circuit commands the drive circuit and transducer to apply a succession of monitoring ultrasound pulses to a location on the cornea after termination of the push pulse, while the cornea is rebounding, and to acquire signals representing the ultrasound reflected from such location responsive to each monitoring pulse. The monitoring pulses may be applied to the same location as the push pulse, or to a different location. Where the device depicted in FIGS. 1 and 2 is employed, the same transducer used to form the push pulse is also used to provide the monitoring pulses, and thus the monitoring pulses will be applied to the same location as the push pulse. The transverse waves propagating in the cornea will cause the location where the monitoring pulses are applied to move inwardly and outwardly, towards and away from the transducer. This motion will cause a Doppler shift in the frequency of the reflected ultrasound from the monitoring pulses. If the location is moving toward the transducer when the monitoring pulse is reflected, the frequency will be shifted upwardly. If the location is moving away from the transducer, the frequency will be shifted downwardly. The reflected monitoring pulses are received by the transducer and converted to electrical signals. The control circuit acquires a series of frequencies of the reflected monitoring pulses over time. This series will have a periodic variation, and the period of this variation will correspond to the period of the natural vibration of the cornea. This period can be detected, for example, by determining the time between successive maxima or successive minima in the frequency of reflected ultrasound. The frequency of the natural vibration is the inverse of this period.

To facilitate determination of the frequency of the reflected ultrasound, each monitoring pulse desirably has a narrow bandwidth, and thus includes numerous cycles of the ultrasound. Where frequencies such as those discussed above for the push pulse are employed, a narrow-bandwidth pulse can have a duration which is only a small fraction of the period of the natural vibration of the cornea. Therefore, numerous monitoring pulses can be applied during each period of the natural vibration. The relative speed of sound difference between the transverse wave velocity $V_s$ and the longitudinal wave velocity $V_l$ ($V_l > 10 V_s$) means that many monitoring pulses can be launched at (and received from) a single transverse wave as it moves toward and away from the transducer. The monitoring pulses may have lower power than the push pulse.

The control circuit actuates the drive circuit and transducer in the manner discussed above to acquire a period or frequency of the natural vibration as a baseline response of the cornea before commencement of the irradiation, and to acquire a series of additional responses, each including the period or frequency of the natural vibration at a time during the irradiation. Here again, the change in the response is determined, and the control circuit commands the light source to terminate the irradiation when the change reaches a predetermined threshold.

A system and method according to a further embodiment of the invention may use a device and system components as discussed above. In this embodiment, however, the control circuit uses the frequency spectrum of backscattered ultrasound from the cornea as the response of the cornea. He, Xiaoyin and Jun Liu, *A Quantitative Ultrasonic Spectroscopy Method for Noninvasive Determination of Corneal Biomechanical Properties*, Investigative Ophthalmology &

Visual Sci., Vol. 50, No. 11 (November 2009), pp. 5148-54, (hereinafter the "He Article") the disclosure of which is incorporated by reference herein, discusses the use of ultrasonics for the measurement of an aggregate elastic modulus and other physical properties of the cornea. The He Article uses an iterative approach applied to the backscattered power spectra of an ultrasound signal directed at a cornea. The He Article demonstrates that the properties of a cornea prepared in the laboratory can be measured in vitro with a precisely designed (and aligned), acoustic pulse and the requisite signal processing to evaluate changes in spectral content of that acoustic signal as it is reflected from, and transmitted through, the cornea.

Data representing the back scatter power spectrum optionally can be converted to values of corneal materials properties such as aggregate elastic modulus. One or more of these values, or a combination of these values, may serve as the response of the cornea which is used as a proxy for the material properties. Alternatively, the spectral data can be can be used as the response or proxy for the materials properties. Here again, a baseline value of the response is obtained before the irradiation step, and one or more additional values of the response are obtained during irradiation. The control circuit terminates the irradiation when the change in the response reaches a predetermined threshold.

The He Article endeavors to determine the absolute material properties of the cornea, comparing the acoustic power spectra determined results against direct measurements by iterating through established models of wave propagation and absorption as a function of frequency. However, He's acoustic processes is based on an idealized analytical approach that is not exceedingly easy to translate to a clinical environment. For example, different wavelengths of ultrasound will refract at different angles through interfaces. Therefore, a very slight misalignment of the (assumed) acoustic plane wave and the apex of the curved cornea imparts spectral shifts into the acoustic signature of the pulse that are geometric in origin (as opposed to the material property generated). He's technique requires great care in alignment that is not possible in the clinical setting, even in an on-eye transducer. Thus, in practice, the values of material properties determined using a device and system as discussed above may differ from the true or "absolute" values of these properties.

However, as discussed above, active CCXL dosimetry feedback control does not require the determination of the absolute material properties. Where the difference in the response between the baseline and additional response is employed, the comparison between baseline and additional values will cancel out these systematic errors. To assure such cancellation, it is desirable to use the same transducer or transducers to acquire both the baseline and additional responses, and to keep the transducer or transducers as a whole in a fixed position on the eye throughout the process. Even if the response does not accurately reflect the absolute material properties, the difference between baseline and additional responses will still correlate with the degree of crosslinking.

Stated another way, one method to achieve this "relative" approach is to determine the approximate values of the cornea material properties or proxies for such properties using the He technique, but ignoring the departures from theory in the actual measurement (such as the likely misalignment of the impinging acoustic wave and the cornea and any deviations from a perfect plane wave generated by the transducer). These sources of systematic error will be identical in the both measurements. In one example, change in the acoustic spectrum is used as a proxy for change in corneal material properties. Thus, values representing spectral change are used directly as the look-up values. Theory shows that, all else being equal between two measurements, the material properties determine the power spectral shifts. Thus, the assumed material properties may not have to be determined, as the characteristic of the power spectrum itself may serve as a proxy for the material properties altered by CCXL, and thus as a proxy for the ultimate cornea shape outcome.

The intraocular pressure may influence the responses acquired in the methods discussed above. Thus, changes in the intraocular pressure between the time a baseline response is acquired and the time an additional response is acquired during irradiation may influence the comparison between baseline and additional responses. To further eliminate sources of potential error in the any of the embodiments discussed above, the intraocular pressure may be measured during irradiation. The control circuit may combine the measured intraocular pressure the measured response of the cornea acquired by any of the methods discussed above to produce a "composite proxy value" that incorporates both mechanical properties changes and pressure-induced shape changes. One approach to monitoring the intraocular pressure is to use an on-lens pressure sensor system similar to Mansouri (Mansouri et. al., *A Minimally Invasive Device for the Monitoring of* 24-*hour Intraocular Pressure Patterns*, U.S. Ophthalmic Review 6(1):10-14 (2013), the disclosure of which is incorporated by reference herein.

In the embodiments discussed above, the transducer is a single-element transducer. However, for monitoring treatment of certain complex conditions such as some astigmatisms, a more complex transducer arrangement may be used. The transducer may be fabricated as a two-dimensional ("2D") ultrasonic array. Such an array can be used to provide measurements at multiple locations on the cornea. For example, multiple measurements may be used where different doses of UV are delivered to different locations on the cornea is a complex or custom CCXL correction. In one embodiment, the 2D array of transducer elements are patterned to match a 2D array of masking elements used to block the UV in certain region to affect a specific corneal shape change.

In a 2D ultrasonic array to control CCXL, the individual elements would not necessarily have to be physically separated from each other (mechanically isolated to prevent acoustic crosstalk as is done in imaging transducer by creating fine slices between elements). The elements could simply be defined by patterning individual electrodes on one of the surfaces of a unitary piezoelectric element as, for example, by screen printing the individual electrodes. In one embodiment, the front electrode 50 shown in FIG. 2 may serve as the common (ground) electrode for the transducer elements so as to provide an unbroken reflector for UV light. In this embodiment, the backing element 52 would be made from a non-conductive material to maintain electrical isolation. The rear or outwardly-facing surface of the piezoelectric film 48 would be provided with a 2D array of individual electrodes, and each such individual electrode would be separately connected to the drive circuit.

The elements of a 2D array can be individually excited and "read" through the addressable electrodes, whether disposed on the front surface or rear surface of the piezoelectric material. The individual electrodes are electrically isolated from one another using a patterned conductor created with a technique such as screen printing. One method to connect to these rear addressable electrode is to pattern a fine conductive lead to each element, allowing electrical access to each element (including those "interior" to the array) from outside the footprint of the array. Alternatively, the elements could be accessed by some type of electrical via system that either penetrates the backing layer, or is incorporated as part of the backing layer.

The ability to pattern acoustic elements (as opposed to slicing to separate individual elements) is possible for two reasons. First, piezo-plastics tend to be very lossy, thus they attenuate energy rapidly, and prevent the acoustic excitement through shear waves of an area much larger than the area excited electronically (they are also lossy to compressional waves, helping with creation of a broadband signal). Acoustic isolation will confine the collection of pixel dosimetry data (i.e., data collected separately for each individual location on the cornea) to roughly only the pixel in question (i.e., the location aligned with the individual emitting element). Even with a lossy material between elements, some crosstalk between elements of the array is probable. However, unlike imaging systems, the elements of the 2D acoustic dosimetry array would be driven with time multiplexing, meaning that they would be excited one at time. In this sense, it is not truly an "acoustic array," but rather a collection of individual elements. Imaging systems drive all the elements of the acoustic array at the same time, shifted only slightly in phase to affect beam steering. Crosstalk is a significant problem for steered beams, but will have negligible effect on a 2D "collection of elements" for dosimetry data collection.

In one method of manufacturing the transducer 47 shown in FIGS. 1 and 2, lightly backed plastic transducer, microballoons, either conductor-coated or non-conductive, are mixed with an adhesive matrix that may be a conductive (silver loaded) epoxy, or some other adhesive, or a combination thereof, to obtain the target light, attentive set of properties. Once cured, this foam is then processed into sub-millimeter layer that is adhered to the piezoelectric layer using one of a few possible methods. One approach to bonding the foam layer is to use a non-uniform pressure technique after E. Papadakis (U.S. Pat. No. 3,664,902) to achieve the extremely thin bond lines required in high frequency ultrasound. Another technique is to adhere only an annular ring outside of the active area, allowing a thin air layer that may further control back reflections. Creating a bond outside of the active area can be done by making the rear electrode on the piezoelectric layer (the electrode that will be in contact with the foam) larger than the front electrode, and adhering the foam around this extra perimeter, with potentially a few other small conductive contact points across the active area. Finally, this entire acoustic stack can be thermally and/or mechanically formed to obtain the desired curvature. It can then be assembled to the housing 32 along with the active components of the UV delivery system.

In the embodiments discussed above, the acoustic dosimetry elements are mounted in an on-eye CCXL device. However, this is not essential. An on-eye device incorporating acoustic dosimetry elements can be positioned on the eye and light such as UV light effective for crosslinking can be applied to the eye by an external or "standoff" light-applying device. In this case, the on-eye device may have an opening or transparent area for transmission of the light from the light-applying device to the eye.

In the embodiment discussed above with reference to FIGS. 1 and 2, the irradiation is applied to a circular region at the center of the cornea, and the ultrasonic transducer is aimed at this region. This arrangement is used to treat myopia. Where the irradiation is intended to treat hyperopia, the irradiation may be applied to an annular region of the cornea. In this case, the ultrasonic transducer or transducers desirably are aimed at the annular region.

In the embodiment discussed above with reference to FIGS. 1 and 2, a single transducer is used to transmit and receive all of the ultrasonic energy used in acquiring the responses of the cornea. However, the device may include plural transducers. For example, a device using the natural vibration frequency as the response may include one transducer for applying the push pulses, another transducer for applying the monitoring pulses, and yet another transducer for receiving the reflected monitoring pulses. In yet another arrangement, the monitoring pulses may be replaced by continuous monitoring ultrasound emitted by one transducer, with the reflected ultrasound being received by another transducer.

The features of the individual embodiments discussed above may be combined with one another. For example, measurements of the transmission time of ultrasound may be used in conjunction with measurements of the natural frequency or period of vibration of the cornea. Likewise, measurement of the spectrum of backscattered ultrasound can be combined with one or more of the other modalities discussed above. For example, the various responses can be combined with one another to yield a composite value, and that value can be used as a proxy for the material properties of the cornea.

In the embodiments discussed above, the change in the response of the cornea is determined by comparing additional and baseline responses. However, the techniques and systems discussed above also can be used to acquire individual measurements of material properties of the cornea, without using the comparison technique.

The following paragraphs further describe certain aspects of the invention:

A method of measuring the physical properties of a cornea in the eye of a living subject comprising:

(a) mechanically exciting the cornea;

(b) monitoring vibrations of the cornea after termination of the excitation; and (c) determining a natural period or frequency of vibration of the cornea based on the monitoring.

A method as recited in paragraph [0059] wherein the step of mechanically exciting the cornea includes applying a force to the cornea having a component perpendicular to the surface of the cornea.

A method as recited in paragraph [0060] wherein the step of applying a force includes directing a push pulse of excitation ultrasonic energy into the anterior surface of the cornea so that the excitation ultrasonic energy deflects the cornea from a steady state position.

A method as recited in paragraph [0061] wherein the step of monitoring vibrations includes directing monitoring ultrasonic energy toward the anterior surface of the cornea and detecting reflected monitoring ultrasonic energy.

A method as recited in paragraph [0061] wherein the step of monitoring vibrations further includes determining a Doppler shift in the reflected monitoring ultrasonic energy.

A method as recited in paragraph [0062] or paragraph [0061] wherein the monitoring ultrasonic energy has a frequency of at least 20 MHz.

A method as recited in paragraph [0062] or paragraph [0063] wherein the monitoring ultrasonic energy has a frequency of at least 50 MHz.

A method as recited in paragraph [0062] or paragraph [0063] wherein the monitoring ultrasonic energy has a frequency of at least 100 MHz.

A method as recited in paragraph [0062] wherein the step of determining a natural period or frequency of vibrations of the cornea includes determining a time between a maximum positive Doppler shift and a maximum negative Doppler shift in the reflected monitoring ultrasonic energy.

A method as recited in paragraph [0062] wherein at least two of the steps of directing an excitation pulse, directing monitoring ultrasonic energy and detecting reflected monitoring ultrasonic energy are performed using a single ultrasonic transducer.

A method as recited in paragraph [0068] wherein all three of the steps of directing an excitation pulse, directing monitoring ultrasonic energy, and detecting reflected monitoring ultrasonic energy are performed using a single ultrasonic transducer.

A method as recited in paragraph [0062] wherein the step of directing monitoring ultrasonic energy includes directing a succession of pulses of monitoring ultrasonic energy toward the anterior surface of the cornea.

A method as recited in any of paragraphs [0062]-[0069] wherein the step of directing monitoring ultrasonic energy includes directing continuous wave ultrasonic energy toward the anterior surface of the cornea from a first transducer and the step of detecting the reflected ultrasonic energy is performed using a second transducer.

A method as recited in any of paragraphs [0061]-[0063] wherein the excitation ultrasonic energy has a frequency of 20 MHz or more.

A method as recited in any of paragraphs [0061]-[0063] wherein the excitation ultrasonic energy has a frequency of 50 MHz or more.

A method as recited in any of paragraphs [0061]-[0063] wherein the excitation ultrasonic energy has a frequency of 100 MHz or more.

A method as recited in any of paragraphs [0062]-[0068] further comprising directing brief pulses of ultrasonic energy into the cornea, detecting echoes of the brief pulses from a posterior surface of the cornea, and determining a parameter related to transmission time of the pulses and echoes through the cornea.

A method as recited in paragraph [0075] further comprising detecting echoes of the brief pulses from an anterior surface of the cornea, the step of determining a parameter related to transmission time including determining differences between arrival times of the echoes from anterior and posterior surfaces.

A method as recited in any one of paragraphs [0075] and [0076] wherein the brief pulses and at least one of the monitoring ultrasonic energy and the excitation ultrasonic energy are generated by a single transducer.

A method of corneal crosslinking comprising:
 (a) irradiating the cornea with light to induce crosslinking of collagen in the cornea;
 (b) monitoring the crosslinking by a method as recited in any one of the preceding claims; and
 (c) controlling the irradiating step based at least in part on the natural period or frequency determined in the monitoring step.

A method as recited in paragraph [0078] wherein monitoring step is performed repeatedly and the controlling step includes terminating the irradiating step when the natural frequency or period has changed by a threshold amount.

A method as recited in paragraph [0079] wherein the repetitions of the monitoring step include one or more baseline monitoring steps performed before the irradiating step and the threshold amount is a function of a baseline natural frequency or period determined in the baseline monitoring steps.

A method as recited in any of paragraphs [0078]-[0080] further comprising treating the cornea with an agent which facilitates crosslinking, wherein the irradiating step includes applying light at a wavelength which activates the agent.

A method as recited in any of paragraphs [0078]-[0081] wherein the irradiating step is performed by applying pulses of light and the monitoring step is performed during intervals between pulses.

A method as recited in any of paragraphs [0078]-[0081] wherein the monitoring step is performed while the cornea is being irradiated with light.

A method of monitoring a physical property of the cornea in a living subject comprising:
 (a) applying a structure over the anterior surface of the eye;
 (b) directing brief pulses of ultrasonic energy into the cornea;
 (c) detecting echoes of the brief pulses from a posterior surface of the cornea; and
 (d) determining a transmission time of the pulses and echoes through the cornea.

A method as recited in paragraph [0084] further comprising detecting echoes of the brief pulses from an anterior surface of the cornea, the step of determining a transmission time of the pulses and echoes through the cornea including determining delays between echoes from the anterior surface and echoes from the posterior surface.

A method as recited in paragraphs [0084] or [0085] further comprising applying light to the cornea through the structure, and repeating the determination of transmission time so as to determine a baseline transmission time before commencement of the light applying step and one or more additional transmission times during the light applying step, and determining differences between the additional transmission times and the baseline transmission time.

A method as recited in paragraph [0086] further comprising terminating the light applying step when a difference between an additional transmission time and the baseline transmission time exceeds a threshold value.

A method as recited in paragraph [0087] wherein the threshold value is a function of the baseline transmission time.

A method as recited in paragraph [0088] wherein the threshold value is proportional to the baseline transmission time.

A method of corneal crosslinking comprising irradiating the cornea in the eye of a living subject and simultaneously applying ultrasound to the cornea and determining one or more responses of the cornea to the applied ultrasound.

A method as recited in paragraph [0090] wherein the step of applying ultrasound to the cornea is performed by actuating a transducer mounted on a housing overlying the eye.

A method as recited in paragraph [0091] wherein the step of irradiating the cornea is performed by directing light into a diffuser mounted on the housing.

The invention claimed is:

1. A device for applying irradiation and ultrasound to an eye of a subject comprising:
 (a) a housing having an inwardly-facing surface adapted to rest on an anterior surface of the eye;
 (b) an optical diffuser mounted to the housing, the diffuser having inner and outer surfaces facing inwardly and outwardly; and (c) a ultrasonic transducer mounted to the housing and disposed outward of the diffuser so that the diffuser is disposed between the transducer and the eye when the housing rests on the anterior surface of the eye, wherein the ultrasonic transducer includes a piezoelectric element and a metallic electrode disposed between the piezoelectric element and the diffuser, the metallic electrode being reflective to light.

2. A device as claimed in claim 1 wherein the piezoelectric element is a polymeric piezoelectric film.

3. A device as claimed in claim 2 further comprising a foam backing disposed outward of the polymeric piezoelectric film.

4. A device as claimed in claim 3 wherein the foam backing is electrically conductive.

5. A system for applying irradiation and ultrasound to an eye of a subject comprising:
   (a) a housing having an inwardly-facing surface adapted to rest on an anterior surface of the eye;
   (b) an optical diffuser mounted to the housing, the diffuser having inner and outer surfaces facing inwardly and outwardly; and
   (c) a ultrasonic transducer mounted to the housing and disposed outward of the diffuser so that the diffuser is disposed between the transducer and the eye when the housing rests on the anterior surface of the eye;
   in conjunction with:
   (d) a light source in optical communication with the diffuser;
   (e) a drive circuit connected to the transducer, the drive circuit being operable to actuate the transducer to direct ultrasonic energy into the cornea and derive signals representing ultrasonic energy returned from the cornea; and
   (f) a control circuit connected to the drive circuit and to the light source, the control circuit being operable to repeatedly determine a response of the cornea to the ultrasonic energy based on the signals so as to provide a baseline response before operation of the light source to irradiate the cornea and one or more additional responses during the operation of the light source, compare the additional responses to the baseline response and control operation of the light source based at least in part on the results of the comparison.

\* \* \* \* \*